United States Patent [19]

Gartner et al.

[11] Patent Number: 5,777,167

[45] Date of Patent: Jul. 7, 1998

[54] PROCESS FOR THE REMOVAL OF ODOR FROM REACTION PRODUCT MIXTURES OF ALKYTHIOETHANAMINES AND THEIR ACID SALTS

[75] Inventors: Charles D. Gartner; George A. Paul. both of Midland, Mich.

[73] Assignee: The Dow Chemical Company. Midland, Mich.

[21] Appl. No.: 714,872

[22] Filed: Sep. 14, 1996

[51] Int. Cl.$^6$ ............................................. C07C 209/84
[52] U.S. Cl. .............................. 564/497; 564/501
[58] Field of Search ................ 564/497, 501, 564/296

[56] References Cited

U.S. PATENT DOCUMENTS 4,086,273 4/1978 Berazosky et al. .
4,816,061 3/1989 Walter, Jr. et al. .
4,982,004 1/1991 Relenyi et al. .
5,025,038 6/1991 Relenyi et al. .
5,087,757 2/1992 Mariam et al. .
5,155,131 10/1992 Relenyi et al. .

Primary Examiner—Brian M. Burn
Attorney, Agent, or Firm—S. Preston Jones; James M. Pelton

[57] ABSTRACT

The instant invention is directed to a process for removing odor from alkylthioethylamine reaction product mixtures having said odor. The process comprises first contacting an alkylthioethanamine reaction product mixture with a neutralizing amount of aqueous alkali metal hydroxide to form an organic phase and an aqueous phase. Next, the organic phase is separated from the aqueous phase. After separation, a sufficient amount of an aqueous hydrohalic acid is added to the organic phase to form an alkylthioethanamine hydrohalide which has reduced odor.

23 Claims, No Drawings

PROCESS FOR THE REMOVAL OF ODOR FROM REACTION PRODUCT MIXTURES OF ALKYTHIOETHANAMINES AND THEIR ACID SALTS

FIELD

The present invention is directed to a process for preparing low-odor reaction product mixtures of alkythioethanamines and their acid salts.

BACKGROUND AND SUMMARY OF THE INVENTION

Reaction product mixtures of alkylthioethanamines and their salts are known to be useful as antimicrobials and cleaners in many different applications. The alkylthioethanamine reaction product mixtures may be made commercially by at least two different processes. In one process, a suitable alkene is reacted with a suitable mercaptoethylamine salt, in the presence of a free radical initiator and a suitable solvent to enhance freeze–thaw stability, such as propylene glycol, to form the desired product, i.e., an alkylethylamine salt in admixture with propylene glycol and water. The process is called mercaptan addition and is illustrated by, for example, the following reaction scheme:

$$R^1—CH=CH_2+HS—CH_2—CH_2—NH_2.HX \rightarrow R^1—CH_2—CH_2—S—CH_2—CH_2—NH_2.HX$$

wherein $R^1$ is an alkyl moiety and HX is a suitable acid such as hydrochloric or hydrobromic acid. The process is described in, for example, U.S. Pat. No. 5,087,757, incorporated herein by reference.

Another commercial process of making alkylthioethanamine reaction product mixtures involves reacting a 2-oxazoline and an alkyl mercaptan in the presence of a Lewis acid catalyst to form an amide. The amide is hydrolyzed with an aqueous hydrohalic acid to form an alkylthioethanamine salt. The process is called hydrolysis and illustrated by, for example, the following reaction scheme:

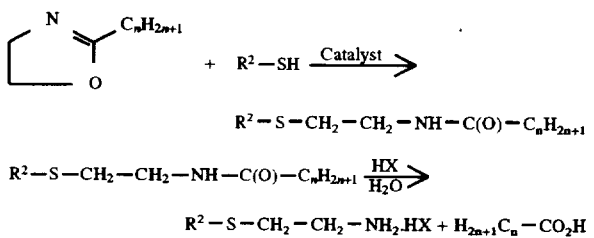

$$R^2—S—CH_2—CH_2—NH—C(O)—C_nH_{2n+1}$$

$$R^2—S—CH_2—CH_2—NH—C(O)—C_nH_{2n+1} \xrightarrow{\frac{HX}{H_2O}}$$

$$R^2—S—CH_2—CH_2—NH_2.HX + H_{2n+1}C_n—CO_2H$$

wherein $R^2$ is an alkyl moiety, n is from about 1 to about 4, and HX is a suitable acid such as hydrochloric or hydrobromic acid. Any remaining HX and a part of the carboxylic acid is then neutralized by contacting the reaction product with aqueous potassium hydroxide. The neutralized reaction product is then diluted with propylene glycol and/or water to give the reaction product freeze–thaw stability. The process is described in, for example, U.S. Pat. Nos. 4,086,273; 4,982,004; and 5,025,038 which are incorporated herein by reference.

U.S. Pat. No. 4,816,061, incorporated herein by reference, teaches that the alkylthioethanamine reaction product mixtures made by the above processes may be used in the treatment of water to control microorganisms and biofouling. Generally, the alkylthioethanamine reaction product mixtures are most effective in water which has a high hardness, an alkaline pH, or both a high hardness and an alkaline pH. Usually, water in cooling towers, paper mills, and recreational pools and spas have both a high water hardness and an alkaline pH. Therefore, in these environments, alkylthioethanamine reaction product mixtures are very effective as antimicrobials to control microorganisms and/or cleaners to control biofouling.

Unfortunately, even though the alkylthioethanamine reaction product mixtures made by the processes described would be effective in controlling microorganisms and/or biofouling in recreational pools and spas, they are not widely utilized. This is due in part to the fact that the reaction product mixtures have an undesirable odor. Fragrances to mask the unpleasant odors of the above alkylthioethanamine reaction product mixtures may be added to said reaction product mixtures. However, the addition of fragrance is costly, may effect the efficacy of the reaction product mixture, and may be objectionable to some consumers. Therefore, it would be desirable to discover a process for removing the odor from reaction product mixtures of alkylthioethanamines and their salts. If this could be accomplished, then alkylthioethanamine reaction product mixtures would become more acceptable for use in applications such as the treatment or cleaning of recreational swimming pools and spas, antimicrobial use in cooling towers and paper mills, and any other application where the odor makes the use of said reaction product mixtures undesirable.

In its broadest aspect, the instant invention is directed to a process for removing odor from alkylthioethylamine reaction product mixtures having said odor. The process comprises:

1) contacting an alkylthioethanamine reaction product mixture with a neutralizing amount of aqueous alkali metal hydroxide to form an organic phase and an aqueous phase;

2) separating the organic phase from the aqueous phase; and then 3) adding a sufficient amount of an aqueous hydrohalic acid to the organic phase to form an alkylthioethanamine hydrohalide having reduced odor.

In another aspect, the instant invention is directed to a process for removing odor from reaction product mixtures of alkylthioethanamine hydrohalide having the formula $R^3—CH_2—CH_2—S—CH_2—CH_2—NH_2.HX$, wherein $R^3$ is a $C_6$–$C_{16}$ alkyl moiety, and HX is a suitable acid, said reaction product mixture being prepared by contacting a compound of the formula $R^3—CH=CH_2$, wherein $R^3$ is as previously defined, with a compound of the formula $HSCH_2—CH_2—NH_2.HX$, wherein HX is as previously defined, in the presence of a solvent of propylene glycol and water and a catalytic amount of a free radical initiator, at a temperature of from about 25° C. to about 300° C., the process for removing odor comprising:

1) contacting the reaction product mixture with a neutralizing amount of aqueous alkali metal hydroxide to form an organic phase and an aqueous phase;

2) separating the organic phase from the aqueous phase; and then 3) adding a sufficient amount of an aqueous hydrohalic acid to the organic phase to form an alkylthioethanamine hydrohalide having reduced odor.

In yet another aspect, the instant invention is directed to a process for removing odor from reaction product mixtures of alkylthioethanamine hydrohalide, said reaction product mixture being made by contacting an amide of the formula $R^4—S—CH_2—CH_2—NH—C(O)—CH_2—CH_3$, wherein $R^4$ represents a straight or branched chain alkyl group of 6 to 16 carbon atoms, with aqueous hydrochloric or hydrobromic acid to form a reaction product mixture comprising alkylthioethanamine hydrohalide and propionic acid, the process for removing odor comprising:

1) contacting the reaction product mixture with a neutralizing amount of aqueous alkali metal hydroxide to form an organic phase and an aqueous phase;

2) separating the organic phase from the aqueous phase; and then 3) adding a sufficient amount of an aqueous hydrohalic acid to the organic phase to form an alkylthioethanamine hydrohalide having reduced odor.

The low-odor product of each of the three processes described above has been discovered to be particularly useful in controlling the fouling of recreational bodies of water, for example, pools and spas. The product is generally used in an effective amount, i.e., an amount needed to keep the body of water substantially clear, clean, and free of microorganisms. This amount is usually at least about 0.1, preferably at least about 1, most preferably at least about 5 parts per million (ppm). This amount is usually less than about 100, preferably less than about 20, most preferably less than about 10 ppm.

DETAILED DESCRIPTION OF THE INVENTION

As used herein "neutralizing amount" is an amount which fully neutralizes the alkylthioethanamine hydrochloride in the reaction product mixture. "Fully neutralizes" means that in a reaction of the alkylthioethanamine hydrohalide with aqueous alkali metal hydroxide substantially all, i.e., at least 90, preferably at least 95, more preferably at least 99 percent, of the alkylthioethanamine hydrohalide is converted to alkylthioethanamine when the reaction reaches equilibrium. Equilibrium is characterized in that the neutralization reaction has reached its equivalence point, i.e., the reaction and its opposite or reverse reaction occur at the same rate. The reaction is characterized by $R^3-CH_2-CH_2-S-CH_2-CH_2-NH_2.HX+AOH \rightarrow R^3-CH_2-CH_2-S-CH_2-CH_2-NH_2+A^+X^-+H_2O$ wherein $R^3$ is a $C_6-C_{16}$ alkyl moiety, HX is hydrobromic or hydrochloric acid, and A is an alkali metal.

As used herein "alkyl group" means a straight or branched chain hydrocarbon group having from about 6 to about 16 carbons which is derived from an alkane by dropping one hydrogen. Alkyl groups generally have the formula $C_nH_{2n+1}$, wherein n is from about 6 to about 16. Examples of alkyl groups include hexyl, heptyl, octyl, nonyl, decyl, undecyl, dodecyl, tridecyl, tetradecyl, pentadecyl, hexadecyl, and branched derivatives thereof. Among preferred alkyl groups are those having from about 8 to about 12 carbons. A particularly preferred alkyl group is a straight chain decyl group.

As used herein "aqueous alkali metal hydroxide" means an alkali metal hydroxide which is dissolved in water.

As used herein "alkali metal" means a metal from Group IA of the periodic table, i.e., lithium, sodium, potassium, etc. Preferably, the alkali metals utilized herein are sodium or potassium. More preferably the alkali metal utilized herein is sodium.

The process for preparing low-odor antimicrobial reaction product mixtures of alkylthioethanamine hydrohalides of the present invention may be utilized upon any alkylthioethanamine reaction product mixture which has odor as a result of odiferous compounds present in the reaction product mixture so long as the odoriferous compound may be neutralized such that it partitions into an aqueous layer. Examples of odoriferous compounds of this type which are often present in alkylthioethanamine reaction product mixtures include mercaptans, for example, mercaptoethylamine salts and alkyl mercaptans, and carboxylic acids having the formula $C_nH_{2n+1}-CO_2H$ wherein n is from about 1 to about 4.

While not wishing to be bound to any particular theory, it is believed that the undesirable odor of the alkylthioethanamine reaction product mixtures results from mercaptan starting materials, i.e., mercaptoethylamine salt in the mercaptan addition process or alkyl mercaptan in the hydrolysis process, which remain in the final alkylthioethanamine products. In addition, the alkylthioethanamine reaction product mixtures made by the hydrolysis process described above also contain a carboxylic acid, such as propionic acid, as a byproduct. It is believed that the carboxylic acid also adds to the undesirable odor of the alkylthioethanamine reaction product mixtures.

In step (1) of the instant process, the alkylthioethanamine hydrohalide is fully neutralized by adding a neutralizing amount of aqueous alkali metal hydroxide to the initial reaction product mixture. It is preferable to add the aqueous alkali metal hydroxide with sufficient agitation to ensure adequate contact between the alkali metal hydroxide and the mixture. The amount of aqueous alkali metal hydroxide sufficient to fully neutralize the initial mixture will vary depending upon the amount and strength of other acidic species which may be present, as well as, the strength of the alkali metal hydroxide employed.

"Acidic species" means those species which are capable of forming hydronium ions in water. Acidic species which may be present and which must be neutralized before the alkylthioethanamine hydrohalide due to the relative strengths of the conjugate bases, may include HCl, HBr, carboxylic acid such as propionic acid, alkylthioethanamine hydrochloride, mercaptans of the formula $R^5-SH$ wherein $R^5$ is $CH_2CH_2NH_2$ or an alkyl moiety, or mixtures thereof. Example of reactions of particular importance for this invention are characterized by $HX+AOH \rightarrow AX+H_2O$ $CH_3CH_2COO-A+AOH \rightarrow CH_3CH2COO^-A^++H_2O$ $R^6-S-CH_2-CH_2-NH_2.HX+AOH \rightarrow R^6-S-CH_2-CH_2-NH_2+AX+H_2O$, and $R^6-SH+AOH \rightarrow R^6-S^-A^++H_2O$ wherein X represents chlorine or bromine, A represents an alkali metal atom, and $R^6$ represents a straight or branched chain alkyl group of 6 to 16 carbon atoms.

The pH after neutralization will depend upon the amoun and types of acidic species initially present as well as the amount and type of alkali metal hydroxide utilized fo neutralization. Typically, the pH will increase to at leas about 9.5, preferably to at least about 10 from an initial pH of from about 0 to about 1.0, when the acids are full neutralized.

Although it is not necessary in most instances, if the concentration of alkylthioethanamine hydrohalide is high i.e., more than about 10, preferably more than about 15 more preferably more than about 40 weight percent of the mixture, then it may be desirable to heat the initial mixtur of acids and alkylthioethanamine hydrohalide to a tempera ture sufficient to reduce the viscosity of the initial mixture By reducing the viscosity of the initial mixture, the mixin of the aqueous alkali metal hydroxide, the acids, and alky lthioethanamine hydrohalide is enhanced which leads t better separation of the organic layer from the aqueous laye in step (2). Suitable viscosity reduction occurs when th mixture is heated to at least 40°, preferably at least 50°, mor preferably at least 70° C. The mixture should not be heated to a temperature so high that the water boils. Therefore, the mixture should not be heated above about 100° C.

After the neutralization of step (1), it is advantageous to allow the subsequently formed mixture to settle, i.e., to not subject it to agitation, for a time sufficient to allow an organic layer and an aqueous layer to form. In this manner, the separation of the organic layer from the aqueous layer is facilitated. The time for which the mixture should be allowed to settle will vary based upon the size and shape of the vessel which contains the mixture, as well as, the volume, contents, and temperature of the mixture. Generally, such time should be at least 5 minutes, preferably at least 15 minutes, more preferably at least 30 minutes.

After the organic layer and aqueous layer have formed and the mixture has settled, substantially all of the alkylthioethanamine will reside in the organic layer, while substantially all of the previously acidic species and a majority of the propylene glycol will reside in the aqueous layer. The organic layer is then separated from the aqueous layer in step (2). The separation, i.e., isolation, of the organic layer from the aqueous layer may be accomplished by any means known in the art. Typical means for separation which may be utilized include distillation, evaporation, extraction, etc. Extraction is convenient and simple and, therefore, particularly preferred.

Many different methods of extracting the organic layer from the aqueous layer may be employed. The most convenient is to employ a vessel which has a means for draining the aqueous layer. Since the aqueous layer resides below the organic layer, the means for draining the aqueous layer will advantageously be at the bottom of the vessel. In this manner, the aqueous layer may be removed by simply utilizing the means for draining and allowing the aqueous layer to flow out of the vessel. The time at which substantially all of the aqueous layer has been removed may be determined visually if the vessel is transparent. Another way of determining when substantially all of the aqueous layer has been removed is via a conductance probe. A conductance probe is capable of measuring the electrical resistance of a liquid as it exits the vessel. By employing this probe, one may determine the point at which the liquid being drained from the vessel changes from aqueous to organic.

Although it is generally not necessary, if the odor is particularly objectionable, i.e., high odor, it may be necessary to repeat steps (1) and (2). In this manner, the odoriferous, water-miscible compounds that remain in the organic layer may be moved to an aqueous layer and removed. It is believed that some of the propylene glycol, i.e., less than about ½, preferably less than about ⅓, more preferably less than about ¼ of the initial propylene glycol, remains in the organic layer because the alkylthioethanamine acts as a surfactant and solubilizes the propylene glycol. In turn, the propylene glycol which remains in the organic layer may enhance the solubility of the odoriferous compounds within the organic layer making it necessary to repeat steps (1) and (2).

After the separation of the organic layer from the aqueous layer in step (2), a sufficient amount of aqueous hydrochloric or hydrobromic acid is then added to the organic phase to form alkylthioethanamine hydrohalide wherein the hydrohalide is hydrochloride or hydrobromide. The amount of hydrochloric or hydrobromic acid which is added should be sufficient to cause the alkylthioethanamine to form an aqueous solution of alkylthioethanamine hydrohalide. By "aqueous solution of alkylthioethanamine hydrohalide" is meant that substantially all, i.e., at least 80, preferably at least 90, more preferably at least 99, weight percent of alkylthioethanamine is in its salt form. Therefore, an organic layer having alkylthioethanamine and an aqueous layer having alkylthioethanamine hydrohalide are not both present. Generally, at least about 0.8, preferably at least about 0.9, more preferably at least about 1.0 equivalents of acid are added per equivalent of alkylthioethanamine present. While not wishing to be bound to any theory, it is believed that less than 1.0 equivalent of acid may be usefully employed because the alkylthioethanamine hydrohalide which is formed acts as a surfactant to bring any additional alkylthioethanamine into solution. On the other hand, the amount of hydrochloric or hydrobromic acid which is added should not be so much that a very acidic, corrosive alkylthioethanamine hydrohalide results. Generally, no more than about 1.2, preferably no more than about 1.05, more preferably no more than about 1.01 equivalents of hydrochloric or hydrobromic acid per equivalent of alkylthioethanamine are added.

Freeze–thaw stability of the low-odor alkylthioethanamine reaction product of this invention may be desired in some applications. If freeze–thaw stability of the reaction product mixture is desired, then following the addition of the acid, propylene glycol and water may be added, as discussed in, for example, U.S. Pat. No. 5,025,038, incorporated herein by reference. Such reaction product mixtures remain homogeneous at room temperature even after being subjected to freeze–thaw transitions. Optionally, surfactants and antifoam agents may also be added to the reaction product mixtures of this invention.

The following examples are provided to illustrate the present invention and the manner in which it may be practiced, but as such are not to be construed as limitations on the overall scope thereof. All percentages in the examples are by weight unless specified otherwise.

EXAMPLE 1

Reaction product mixture A, which was made by a hydrolysis process as described in, for example, U.S. Pat. Nos. 4,086,273; 4,982,004; and 5,025,038, incorporated herein by reference, contained 65 weight percent (%) water, 14.9% 2-(n-decylthio) ethanamine (DTEA), 3.9% propionic acid, 1.0% potassium propionate, 14.9% propylene glycol, and 0.4% others. 203 kilograms (kg) of Reaction product mixture A was heated to approximately 40° C. 16.5 kg of 50% sodium hydroxide was added to the Reaction product mixture A while stirring to bring the pH to 10.5 and form a mixture. The mixture was allowed to settle for two hours in order that an aqueous lower layer and an organic top layer were formed. The aqueous layer was decanted off and the organic layer retained. 75 kg of tap water was added to the organic layer in conjunction with 90 grams of a food grade silicone antifoaming agent (Dow Corning FG-10). 7.24 kg of 37% HCl and a quantity of water was added to bring the reaction product mixture to a final weight of 195 kg and a pH of 5. The final product, Reaction product mixture B, contained 81.7% water, 15.2% DTEA.HCL, 0.7% propionic acid and sodium propionate combined, 2% propylene glycol, and 0.4% others.

EXAMPLE 2

A sample of Reaction product mixture A and a sample of Reaction product mixture B were tested for odor by 19 people. Each of the 19 people smelled Reaction product mixture A and Reaction product mixture B. Twelve of the 19 people preferred Reaction product mixture B. Five of the 19 people preferred Reaction product mixture A. Two of the 19 people could not detect a difference between Reaction product mixture A and Reaction product mixture B.

EXAMPLE 3

Reaction product mixture A was diluted by adding 99 parts water per part of Reaction product mixture A to form Reaction product mixture C. Reaction product mixture B was diluted by adding 99 parts water per part of Reaction product mixture B to form Reaction product mixture D. A sample of Reaction product mixture C and a sample of Reaction product mixture D were tested for odor by 21 people. Each of the 21 people smelled Reaction product mixture C and Reaction product mixture D. Fifteen of the 21 people preferred Reaction product mixture D. One of the 21 people preferred Reaction product mixture C. Five of the 21 people could not detect a difference between Reaction product mixture C and Reaction product mixture D.

EXAMPLE 4

Reaction product mixture E, which was made by the mercaptan addition process described in, for example, U.S. Pat. No. 5,087,757, incorporated herein by reference, contained 68.8 weight percent (%) water, 15.1% 2-(n-decylthio) ethanamine (DTEA), 0.25% cysteamine hydrochloride, 14.9% propylene glycol, and 1% others. 1.0 kilograms (kg) of Reaction product mixture E was heated to approximately 40° C. 51 grams (g) of 50% sodium hydroxide was added to the Reaction product mixture E while stirring to bring the pH to 10.5 and form a mixture. The mixture was allowed to settle for one hour in order that an aqueous lower layer and an organic top layer were formed. The aqueous layer was decanted off and the organic layer retained. 0.76 kg of tap water was added to the organic layer in conjunction with 59 g of 37% HCl to bring the reaction product mixture to a final weight of 1.0 kg and a pH of 4. The final product, Reaction product mixture F, contained 80% water, 15.0% DTEA.HCL, 4% propylene glycol, less than 0.1% cysteamine hydrochloride, and less than 1% others.

What is claimed is:

1. A process for removing odor from an alkylthioethanamine hydrohalide reaction product mixture having an odor resulting from the presence of odiferous compounds in said reaction product mixture which comprises:
   (1) contacting said alkylthioethanamine reaction product mixture with a neutralizing amount of an aqueous alkali metal hydroxide sufficient to neutralize the alkylthioethanamine hydrohalide and the odiferous compounds therein and to form an organic phase and an aqueous phase;
   (2) separating the organic phase from the aqueous phase; and then
   (3) adding a sufficient amount of an aqueous hydrohalic acid to the organic phase to cause the alkylthioethanamine to form an aqueous solution of alkylthioethanamine hydrohalide having a reduced odor.

2. The process of claim 1 wherein the alkylthioethanamine reaction product mixture comprises alkylthioethanamine hydrohalide and carboxylic acids having the formula $C_nH_{2n+1}$—$CO_2H$ wherein n is from about 1 to about 4.

3. The process of claim 2 wherein the alkylthioethanamine reaction product mixture further comprises hydrochloric acid or hydrobromic acid.

4. The process of claim 3 wherein the alkylthioethanamine reaction product mixture further comprises an alkyl mercaptan.

5. The process of claim 2 wherein the alkylthioethanamine reaction product mixture further comprises propylene glycol.

6. The process of claim 1 wherein the alkylthioethanamine is 2-(n-decylthio) ethanamine.

7. The process of claim 1 wherein the alkali metal hydroxide is sodium hydroxide, potassium hydroxide, or mixtures thereof.

8. The process of claim 1 wherein the hydrohalic acid is hydrobromic acid or hydrochloric acid.

9. The process of claim 1 wherein the alkylthioethanamine reaction product mixture is heated to a temperature of from about 30° C. to about 70° C. before contacting said reaction product mixture with said alkali metal hydroxide.

10. The process of claim 1 wherein the alkylthioethanamine reaction product mixture has a pH of from about 9 to about 11 after contact with the aqueous alkali metal hydroxide.

11. A process for removing odor from an alkylthioethanamine hydrohalide reaction product mixture having an odor resulting from the presence of odiferous compounds in said product mixture wherein the alkylthioethanamine hydrohalide is of the formula R—$CH_2$—$CH_2$—S—$CH_2$—$CH_2$—$NH_2$.HX, wherein R is a $C_6$–$C_{16}$ alkyl moiety, and HX is a suitable acid, said reaction product mixture being prepared by contacting a compound of the formula R—CH=$CH_2$, wherein R is as previously defined, with a compound of the formula HSCH$_2$—$CH_2$—$NH_2$.HX, wherein HX is as previously defined, in the presence of a solvent comprising propylene glycol and water and in the presence of a catalytic amount of a free radical initiator, at a temperature of from about 25° C. to about 300° C., the process for removing said odor and said odiferous compounds comprising:
   (1) contacting said alkylthioethanamine hydrohalide reaction product mixture with a neutralizing amount an aqueous alkali metal hydroxide sufficient to neutralize the alkylthioethanamine hydrohalide and the odiferous compounds therein and to form an organic phase and an aqueous phase;
   (2) separating the organic phase from the aqueous phase and then
   (3) adding a sufficient amount of an aqueous hydrohalic acid to the organic phase to cause the alkylthioethanamine to form an aqueous solution of alkylthioethanamine hydrohalide having a reduced odor.

12. The process of claim 11 wherein the alkylthioethanamine is 2-(n-decylthio) ethanamine.

13. The process of claim 11 wherein from about 0.9 to about 1.2 moles of sodium hydroxide per mole of alkylthioethanamine is contacted with the reaction product mixture of alkylthioethanamine hydrohalide in step (1).

14. The process of claim 11 wherein the hydrohalic acid is hydrobromic acid or hydrochloric acid.

15. The process of claim 11 wherein the alkylthioethanamine reaction product mixture is heated to a temperature of from about 30° C. to about 70° C. before contacting said reaction product mixture with said alkali metal hydroxide.

16. A process for removing odor from an alkylthioethanamine hydrohalide reaction product mixture having an odor resulting from the presence of odiferous compounds in said alkylthioethanamine hydrohalide product mixture, said reaction product mixture being made by contacting an amide of the formula R—S—$CH_2$—NH—C(O)—$CH_2$—$CH_3$ wherein R represents a straight or branched chain alkyl group of 6 to 16 carbon atoms, with aqueous hydrochloric or hydrobromic acid to form a reaction product mixture comprising alkylthioethanamine hydrohalide and propionic acid the process for removing the odor and said odiferous compounds comprising:

(1) contacting said alkylthioethanamine hydrohalide reaction product mixture with a neutralizing amount an aqueous alkali metal hydroxide sufficient to neutralize the alkylthioethanamine hydrohalide and the odiferous compounds therein and to form an organic phase and an aqueous phase;

(2) separating the organic phase from the aqueous phase; and then (3) adding a sufficient amount of an aqueous hydrohalic acid to the organic phase to cause the alkylthioethanamine to form an alkylthioethanamine hydrohalide having a reduced odor.

17. The process of claim 16 wherein the alkylthioethanamine is 2-(n-decylthio) ethanamine.

18. The process of claim 16 wherein from about 1.9 to about 2.3 moles of sodium hydroxide per mole of propionic acid is contacted with the reaction product mixture of alkylthioethanamine hydrohalide in step (1).

19. The process of claim 16 wherein the hydrohalic acid is hydrobromic acid or hydrochloric acid.

20. The process of claim 17 wherein the alkylthioethanamine reaction product mixture is heated to a temperature of from about 30° C. to about 70° C. before contacting said reaction product mixture with said alkali metal hydroxide.

21. A method for controlling fouling in a recreational body of water which comprises contacting the body of water with an effective amount of an alkylthioethanamine hydrohalide reaction product from which odor resulting from the presence of odiferous compounds contained therein has been removed in a process which comprises:

(1) contacting said alkylthioethanamine hydrohalide reaction product mixture having an odor and odiferous compounds presence therein with a neutralizing amount of an aqueous alkali metal hydroxide sufficient to neutralize the alkylthioethanamine hydrohalide and the odiferous compounds therein to form an organic phase and an aqueous phase;

(2) separating the organic phase from the aqueous phase; and then (3) adding a sufficient amount of an aqueous hydrohalic acid to the organic phase to form an alkylthioethanamine hydrohalide having a reduced odor.

22. The method of claim 21, wherein the alkylthioethanamine is 2-(n-decylthio)ethanamine.

23. The method of claim 21 wherein the effective amount is from about 0.1 to about 100 parts per million.

* * * * *